(12) United States Patent
Houston

(10) Patent No.: US 6,576,610 B1
(45) Date of Patent: Jun. 10, 2003

(54) USE OF A CONTEXT-DEPENDENT FUNCTIONAL ENTITY TO ENHANCE THE EFFICACY OF AN AGENT

(75) Inventor: L. L. Houston, Del Mar, CA (US)

(73) Assignee: Nuvas, LLC, San Diego, CA (US)

( * ) Notice: Subject to any disclaimer, the term of this patent is extended or adjusted under 35 U.S.C. 154(b) by 0 days.

(21) Appl. No.: 09/411,067

(22) Filed: Oct. 4, 1999

(51) Int. Cl.[7] .......................... A61K 38/00; C07K 17/00
(52) U.S. Cl. ......................... 514/12; 530/300; 530/324; 530/350; 530/380
(58) Field of Search ................... 514/12; 530/324, 530/300, 380

(56) References Cited

U.S. PATENT DOCUMENTS

| | | | |
|---|---|---|---|
| 5,110,730 A | 5/1992 | Edgington et al. | 435/69.6 |
| 5,206,347 A | 4/1993 | Ruoslahti et al. | 530/413 |
| 5,314,695 A | 5/1994 | Brown | 424/250 |
| 5,433,955 A | * 7/1995 | Bredehorst | 514/55 |
| 5,622,699 A | 4/1997 | Ruoslahti et al. | 424/93.6 |
| 5,801,146 A | 9/1998 | Davidson | 514/12 |
| 5,877,289 A | 3/1999 | Thorpe et al. | 530/387.1 |

FOREIGN PATENT DOCUMENTS

| WO | WO 97/41824 | * 11/1997 |
|---|---|---|
| WO | WO 99/32143 | 7/1999 |

OTHER PUBLICATIONS

Haung et al., Tumor Infraction in Mice by Antibody–Directed Targeting of Tissue Factor To Tumor Vasculature, Science, 275 (5299); 547–550, Jan. 1997.*

Lake et al., "Generation of Diverse Single–Chain Proteins Using a Universal (Gly3–Ser)4 Encoding Oligonucleotide" Bio Techniques, 19 (5): 700 and 702, 1995.*

Balance, D. J., et al., "A hybrid protein of urokinase growth–factor domain and plasminogen–activator inhibitor type 2 inhibits urokinase activity and binds to the urokinase receptor," *European Journal of Biochemistry*, 207:177–183 (1992).

Cao, Y., et al., "Kringle Domains of Human Angiostatin," *The Journal of Biological Chemistry* 271:29461–29467 (1996).

Chang et al., "The Roles of Factor VII's Structural Domains in Tissue Factor Binding," *Biochemistry* 34:12227–12232 (1995).

Colosi, et al., "Characterization of Proliferin–Related Protein," *Molecular Endocrinology* 2(6):579–586 (1988).

Denekamp, J., "Vasculature as a Target for Tumour Therapy," *Prog. appl. Microcir.* 4:28–38 (1984).

Denekamp, J., "Vascular attack as a therapeutic strategy for cancer," *Cancer and Metastasis Reviews* 9:267–282 (1990).

Dvorak, et al., "Structure of Solid Tumors and Their Vasculature: Implications for Therapy with Monoclonal Antibodies," *Cancer Cells* 3(3):77–85 (1991).

Gilbert and Baleja, "Membrane–Binding Peptide from the C2 Domain of Factor VIII Forms an Amphipathic Structure As Determined by NMR Spectroscopy," *Biochemistry* 34(9):3022–3031 (1995).

Goodson, et al., "High–affinity urokinase receptor antagonists identified with bacteriophage peptide display," *Proc. Natl. Acad. Sci. USA* 91:7129–7133 (1994).

Guo, et al., "Interactions of a Laminin–binding Peptide from a 33–kDa Protein Related to the 67–kDa Laminin Receptor with Laminin and Melanoma Cells Are Heparin–dependent," *The Journal of Biological Chemistry* 267(25):17743–17747 (1992).

Guo, et al., "Heparin– and sulfatide–binding peptides from the type I repeats of human thrombospondin promote melanoma cell adhesion" *Proc. Natl. Acad. Sci USA* 89:3040–3044 (1992).

Huang, et al., "Tumor Infarction in Mice by Antibody–Directed Targeting of Tissue Factor to Tumor Vasculature," *Science* 275(5299):547–550 (1997).

Lake, D. F., et al., "Generation Of Diverse Single–Chain Proteins Using a Universal (Gly3–Ser)4 Encoding Oligonucleotide," *Bio Techniques* 1995 19(5):700 and 702.

Lee and Nathans,"Proliferin Secreted by Cultured Cells Binds to Mannose 6–Phosphate Receptors," *The Journal of Biological Chemistry* 263(7):3521–3527 (1988).

O'Reilly, et al., "Angiostatin: A Novel Angiogenesis Inhibitor That Mediates the Suppression of Metastases by a Lewis Lung Carcinoma," *Cell* 79(2):315–328 (1994).

O'Reilly et al., "Endostatin: An Endogenus Inhibitor of Angiogenesis and Tumor Growth," *Cell* 88(2):277–285 (1997).

Pegram, et al., "Inhibitor effects of combinations of HER–2/neu antibody and chemotherapeutic agents used for treatment of human breast cancers," *Oncogene* 18:2241–2251 (1999).

(List continued on next page.)

Primary Examiner—Christopher S. F. Low
Assistant Examiner—Roy Teller
(74) Attorney, Agent, or Firm—Gray Cary Ware & Freidenrich; Lisa A. Haile; Richard J. Imbra

(57) ABSTRACT

The present invention relates to a method of enhancing the efficacy of one or more agents in a subject by administering the agent or agents and a context-dependent functional entity to the subject, wherein a context-dependent functional entity includes a substructure with thrombogenic potential operably linked to a selective recognition domain, and interacts with a function-forming context expressed by a cell or tissue in the subject. The invention also relates to a method of treating a pathologic condition in a subject by administering to the subject a therapeutic agent and a context-dependent functional entity. The invention further relates to a pharmaceutical composition, which contains an agent and a context-dependent functional entity in a pharmaceutically acceptable form. The invention further provides a peptide having the amino acid sequence Pro-Arg-Lys-Leu-Tyr-Asp (SEQ ID NO: 1).

24 Claims, 2 Drawing Sheets

OTHER PUBLICATIONS

Rao and Rapaport, "Activation of factor VII bound to tissue factor: A key early step in the tissue factor pathway of blood coagulation," *Proc. Natl. Acad. Sci. USA* 85:6687–6691 (1988).

Ruf, et al., "Phospholipid–independent and –dependent Interactions Required for Tissue Factor Receptor and Cofactor Function," *The Journal of Biological Chemistry* 266(4):2158–2166 (1991).

Tait, et al., "Prourokinase–Annexin V Chimeras," *The Journal of Biological Chemistry* 270(37):21594–21599 (1995).

Tolsma, et al., "Peptides Derived from Two Separate Domains of the Matrix Protein Thrombospondin–1 Have Anti–Angiogenic Activity," *The Journal of Cell Biology* 122:(2):497–511 (1993).

* cited by examiner

SEQUENCE LISTING

```
<160> NUMBER OF SEQ ID NOS: 5

<210> SEQ ID NO 1
<211> LENGTH: 6
<212> TYPE: PRT
<213> ORGANISM: Homo sapiens

<400> SEQUENCE: 1

Pro Arg Lys Leu Tyr Asp
1               5

<210> SEQ ID NO 2
<211> LENGTH: 17
<212> TYPE: PRT
<213> ORGANISM: Homo sapiens

<400> SEQUENCE: 2

Ala Gly Pro Met Pro His Ser Leu Asn Phe Ser Gln Tyr Leu Trp Tyr
1               5                   10                  15

Thr

<210> SEQ ID NO 3
<211> LENGTH: 15
<212> TYPE: PRT
<213> ORGANISM: Artificial sequence
<220> FEATURE:
<223> OTHER INFORMATION: Spacer element

<400> SEQUENCE: 3

Gly Gly Gly Gly Ser Gly Gly Gly Gly Ser Gly Gly Gly Gly Ser
1               5                   10                  15
```

-continued

```
<210> SEQ ID NO 4
<211> LENGTH: 100
<212> TYPE: PRT
<213> ORGANISM: Artificial sequence
<220> FEATURE:
<223> OTHER INFORMATION: Spacer element
<220> FEATURE:
<221> NAME/KEY: REPEAT
<222> LOCATION: (1)..(5)
<223> OTHER INFORMATION: Spacer peptide variation; sequence repeated
      "n" times, where n = 1-20

<400> SEQUENCE: 4

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 5
<211> LENGTH: 100
<212> TYPE: PRT
<213> ORGANISM: Artificial sequence
<220> FEATURE:
<223> OTHER INFORMATION: Spacer element
<220> FEATURE:
<221> NAME/KEY: REPEAT
<222> LOCATION: (1)..(5)
<223> OTHER INFORMATION: Spacer peptide variation; sequence repeated
      "n" times, where n = 1-20

<400> SEQUENCE: 5

Ser Ser Ser Ser Gly Ser Ser Ser Ser Gly Ser Ser Ser Ser Gly Ser
1               5                   10                  15

Ser Ser Ser Gly Ser Ser Ser Ser Gly Ser Ser Ser Ser Gly Ser Ser
            20                  25                  30

Ser Ser Gly Ser Ser Ser Ser Gly Ser Ser Ser Ser Gly Ser Ser Ser
        35                  40                  45

Ser Gly Ser Ser Ser Ser Gly Ser Ser Ser Ser Gly Ser Ser Ser Ser
    50                  55                  60

Gly Ser Ser Ser Ser Gly Ser Ser Ser Ser Gly Ser Ser Ser Ser Gly
65                  70                  75                  80

Ser Ser Ser Ser Gly Ser Ser Ser Ser Gly Ser Ser Ser Ser Gly Ser
                85                  90                  95

Ser Ser Ser Gly
            100
```

USE OF A CONTEXT-DEPENDENT FUNCTIONAL ENTITY TO ENHANCE THE EFFICACY OF AN AGENT

BACKGROUND OF THE INVENTION

1. Field of the Invention

The present invention relates generally to medical procedures and more specifically to methods of using a context-dependent functional entity to enhance the efficacy of one or more agents in a subject.

2. Background Information

Although cancer remains a leading cause of morbidity and mortality in the world, it appears that more efficacious drugs and treatment protocols are providing increased hope that many, if not all, cancers eventually will be treatable. In some cases, the advances in treatment are due to improved surgical techniques or improved methods of radiation therapy. Advances also have been due to the identification of one or more drugs that are particularly effective for treating cancer. Taxol®, for example, which is a natural product prepared from the Pacific yew tree, can prolong survival of patients with ovarian cancer, which has a very low survival rate. Platinol®, which is a cis-platinum product, is effective in treating metastatic testicular cancer, and also is indicated in bladder cancer that has progressed to a stage that no longer can be treated by surgery.

Further advances in cancer therapy have been made by combining therapies, including surgery and radiation therapy, surgery and drug therapy, radiation therapy and drug therapy, and combined drug therapies. Where feasible, surgery often is used initially to remove the bulk of a tumor, then radiation therapy or chemotherapy is used to kill cells that may be outside of the region of surgery, including metastatic lesions. Treatment of a cancer patient with a drug such as hydroxyurea, which appears to inhibit DNA synthesis in cells, sensitizes the inhibited cells, including cancer cells, to the effects of radiation and, therefore, often is combined with radiation therapy.

Where surgery or radiation therapy cannot provide a significant treatment modality due, for example, to the location or extent of a cancer, combined drug modalities often are the treatment of choice. Generally, drugs are combined based on their having different mechanisms of action. Thus, an antimetabolite, which kills cancer cells by inhibiting DNA synthesis, can be combined with an agent that kills cells by inhibiting cell division. Such combined modalities generally have an additive effect due to each of the agents killing a population of cells sensitive to the drug.

Occasionally, combined modalities can result in a greater than additive effect. For example, treatment with Herceptin®, which is a monoclonal antibody that recognizes a particular cell surface receptor expressed on breast cancer cells, in combination with two chemotherapeutic agents, kills a greater number of cells than would be expected due to simple additive effects. Where combined modality treatment results in a greater than additive effect of cancer cell killing, the dose of each drug often can be reduced. The ability to reduce the doses of chemotherapeutic agents, while still maintaining a therapeutic effect against a cancer, provides a significant therapeutic benefit, since it is the toxic side effects of cancer chemotherapeutic agents to normal cells that often limits the dose of drug that can be administered to a patient and, therefore, limits the treatment. By decreasing the amounts of drugs that need to be administered to a patient to effectively treat a cancer, side effects such as bone marrow depletion, loss of appetite, and hair loss are less severe, thereby improving the patient's quality of life.

Agents such as Herceptin®, which, when combined with other agents, enhance the efficacy of a second drug by producing a greater effect than otherwise would be expected, would be particularly useful for treating diseases such as cancer. Unfortunately, few agents that generally produce such an effect have been identified. Thus, a need exists to identify agents that can be administered, for example, in combination with one or more therapeutic drugs and increase the effectiveness of the drugs. The present invention satisfies this need and provides additional advantages.

SUMMARY OF THE INVENTION

The present invention relates to a method of enhancing the efficacy of one or more agents in a subject by administering to the subject the agent or agents and a context-dependent functional entity ("CDFE"). A CDFE is a chimeric molecule that is composed of modular components and that acts as an integrated unit, which exhibits a functional activity in a position and orientation dependent manner. A CDFE can interact with a function-forming context expressed on a cell or in a tissue in the subject and, as disclosed herein, enhance the efficacy of an agent administered with the CDFE in a subject.

The modular components of a CDFE include a substructure with thrombogenic potential operably linked to a selective recognition domain. The substructure with thrombogenic potential can be a coagulation factor, for example, a vertebrate tissue factor (TF) or a modified form of TF such as a peptide portion of TF having thrombogenic potential. The selective recognition domain can be a kringle domain, for example, a plasminogen kringle 5 domain, or a peptide portion thereof such as the amino acid sequence Pro-Arg-Lys-Leu-Tyr-Asp (SEQ ID NO: 1); or can have, for example, the amino acid sequence as set forth in SEQ ID NO: 2. The substructure with thrombogenic potential is operably linked to the selective recognition domain, or other modular component, either directly or through a spacer element.

A CDFE can interact with a function-forming context expressed on the surface of a cell or in a tissue in the subject, for example, in vascular tissue such as tumor associated vascular tissue, thereby enhancing the efficacy of one or more agents at the site of the cell or tissue. The agent can be, for example, a diagnostic agent, a nutritional molecule, a toxin, a radiation sensitizer, or a therapeutic agent such as a cancer chemotherapeutic agent or other agent or combination of agents, and can be in an encapsulating matrix such as a liposome, which can be a modified liposome. For example, a method of the invention can include administering a cancer chemotherapeutic agent such as doxorubicin, which may or may not be encapsulated in a modified liposome, and a CDFE, either in combination or sequentially in any order; by any of various routes, including, for example, parenterally, intravenously or orally; systemically or at the site of a tissue in which it is desired to enhance the efficacy of the agent; and the timing of administration of the CDFE and the agent can be varied.

The invention also relates to methods of treating a pathologic condition in a subject by administering to the subject a therapeutic agent and a CDFE, which contains a substructure with thrombogenic potential operably linked to a selective recognition domain, whereby interaction of the CDFE with a function-forming context expressed on a cell or in a tissue in the subject enhances the efficacy of the therapeutic agent in the subject, thereby treating the pathologic condition. The pathologic condition can be a cell proliferative disorder, for example, a neoplasm, which can be benign or malignant. The substructure with thrombogenic potential can be a coagulation factor or a portion thereof, for example, a vertebrate TF or a modified form thereof, and the selective recognition domain can be a kringle domain or a portion thereof. Where the pathologic condition to be treated is a malignant neoplastic disease, the therapeutic agent is a cancer chemotherapeutic agent or a combination of chemotherapeutic agents, for example, an antimetabolite, an alkylating agent, an antitumor antibiotic, a cytokine, a hormone, a hormone antagonist, a nitroso compound, a plant alkaloid, a platinum compound, or the like, and can be encapsulated in a liposome, which can be a modified liposome. Where a subject is to be treated by radiation therapy, a therapeutic agent can be a radiation sensitizing agent.

The invention further relates to pharmaceutical compositions, which contain a CDFE and one or more agents in a pharmaceutically acceptable form, wherein the CDFE comprises a substructure with thrombogenic potential and a selective recognition domain. For example, the CDFE can include a modified form of tissue factor and kringle domain, which can be operably linked through a peptide spacer element. The agent can be a diagnostic agent, a nutritional molecule, a toxin, a radiation sensitizer, a therapeutic agent, or the like, or combinations thereof The invention also provides a peptide having the amino acid sequence Pro-Arg-Lys-Leu-Tyr-Asp (SEQ ID NO: 1). Such a peptide is useful, for example, as a selective recognition domain, which can facilitate an interaction of a CDFE with a function-forming context. Polypeptide sequences containing SEQ ID NO: 1 are encompassed within the claimed invention, provided the polypeptide sequence is not plasminogen or a peptide portion of plasminogen containing SEQ ID NO: 1. In particular, chimeric molecules, including, for example, fusion polypeptides, comprising SEQ ID NO: 1 are encompassed within the invention.

DETAILED DESCRIPTION OF THE INVENTION

Figure 1:
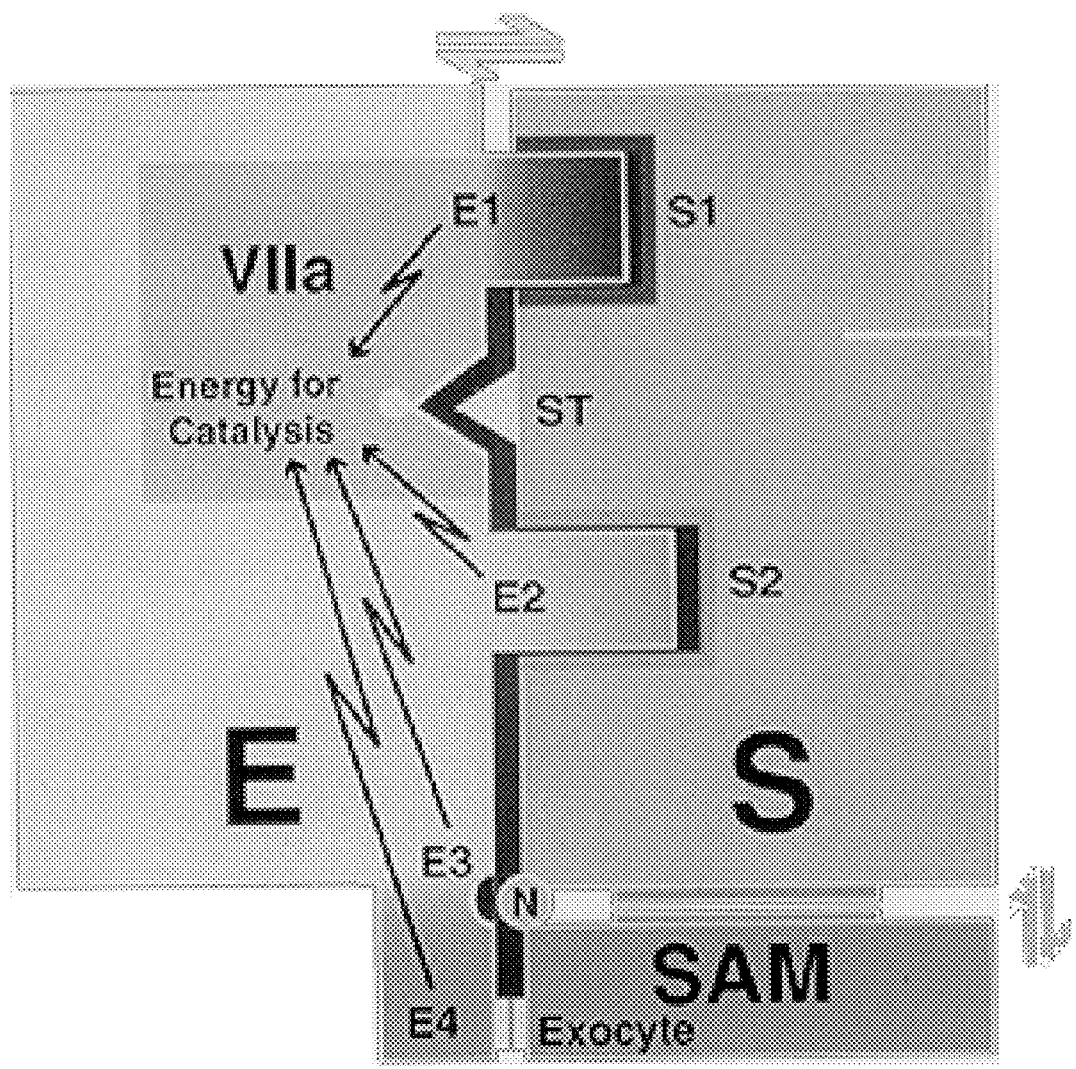
FIG. 1 illustrates an interaction of a context-dependent functional entity (CDFE) and a function-forming context. The CDFE is shown on the left as comprising a modified tissue factor ("E") operably linked to a selective recognition domain (hatched region; see Example I). The function-forming context is shown on the right as comprising a substrate ("S") transiently associated with a surface associated molecule (SAM). E1, E2, E3 and E4 represent exosite recognition domains on the CDFE; S1, S2, N and Exocyte represent complementary exosites on the function-forming context. The CDFE is shown as a complex with blood coagulation factor VIIa ("VIIa"). The double arrows (⇆) indicate that the interactions of S and SAM and of the CDFE and function-forming context are transient. "Energy for catalysis" is provided by the association of the CDFE and function-forming complex, as represented by the single arrows. "ST" indicates the site acted upon by the enzymatic activity of the CDFE:VIIa complex.

The present invention relates to a method of enhancing the efficacy of an agent in a subject by administering to the subject the agent and a context-dependent functional entity (CDFE), which includes a substructure with thrombogenic potential operably linked to a selective recognition domain. A CDFE interacts with a function-forming context expressed on a cell or in a tissue in the subject and enhances the efficacy of one or more agent administered with the CDFE.

A method of the invention is useful, for example, for treating a subject suffering from a pathologic condition by reducing the amount of a therapeutic agent or agents needed to provide a therapeutic effect, or by allowing an administered dose of one or more agents to have a greater efficacy than the agent or agents would have if administered without a CDFE. As such, the invention also provides pharmaceutical compositions, which contain a CDFE and at least one agent, useful for practicing the methods of the invention, and provides medicaments useful for diagnosing or treating a pathologic condition. Context-dependent functional entities are described in PCT/US98/27498 (each reference cited in this application is incorporated herein by reference).

A context-dependent functional entity (CDFE), when administered in combination with a cancer chemotherapeutic agent, enhances the efficacy of the chemotherapeutic agent. The results as disclosed herein demonstrate that a lower dose of one or more therapeutic agents can be administered to a subject to obtain a desired effect than would be necessary if the agent or agents were administered without a CDFE. A method of the invention provides the advantage that potential deleterious side effects due, for example, to administration of a therapeutic agent to a subject are reduced, thereby improving the subject's quality of life without compromising the effectiveness of a treatment.

A CDFE is a non-naturally occurring chimeric molecule that is formed from modular components, which can be naturally or non-naturally occurring, and acts as an integrated unit in a position and orientation dependent manner. As used herein, the term "non-naturally occurring," when used in reference to a CDFE, means that the CDFE is not a product of nature. A chimeric CDFE molecule can be, for example, a fusion polypeptide, a peptide-peptidomimetic conjugate, a peptide-small organic molecule conjugate, or a peptide-nucleic acid conjugate. The term "conjugate" is used specifically herein to mean that the modular components of a CDFE are operably linked. The term "modular components" means at least a substructure with thrombogenic potential and a selective recognition domain. However, a CDFE can include additional modular components including, for example, a spacer element, a tag molecule, or other component that can facilitate preparation or isolation of the CDFE or enhance its functional activity.

A CDFE can be, for example, a chimeric polypeptide that contains a substructure with thrombogenic potential operably linked to a selective recognition domain. One or more components of a CDFE can be modified. For example, a CDFE is exemplified herein by a fusion polypeptide designated NV144, which contains, in part, a modified tissue factor domain operably linked to a peptide portion of plasminogen kringle 5 domain (see Example I).

A CDFE provides a macromolecular recognition surface such that a specific interaction can occur with an appropriate association partner. For exemplary purposes, reference is made herein to a CDFE having an enzymatic potential for a substrate component of a function-forming context. The term "substrate" or "substrate component" is used herein to refer to a component of a function-forming context that is acted upon by a component of a CDFE having enzymatic potential. It should be recognized, however, that a CDFE can have a specific associating activity, for example, for a function-forming context comprising a receptor, a ligand, or the like, in which case the CDFE will have receptor associating potential, ligand associating potential, or the like. A CDFE is described as having a "potential," for example, enzymatic potential, because a CDFE does not exhibit its particular activity unless it is associated with a function-forming context. For example, a CDFE comprising TF or a modified form thereof can act as a cofactor for blood coagulation factor VIIa activity, forming a CDFE:VIIa complex having enzymatic potential for factor X (or factor IX). However, such activity is not exhibited unless the CDFE-:VIIa complex interacts with factor X or factor IX while the factor is reversibly associated with a particular cell surface molecule; such transient association provides a function-forming context that is recognized by the CDFE:VIIa complex with sufficient association energy that catalysis of the substrate can occur.

In general, a CDFE contains a first element (modular component), which can have an enzymatic potential ("substructure with thrombogenic potential" or "enzyme component") or can associate with a molecule to form a complex having a potential, that is operably linked to a second element ("selective recognition domain"), which facilitates the association of the CDFE to a function-forming context. The first element and second element of the CDFE, as well as any additional elements comprising the CDFE, each contribute one or more exosite recognition sites, which together provide a complement of three dimensional conformations that are not present in any single element alone, and that permit transient association and three dimensional orientation of the CDFE with a cognate function-forming element (see, for example, Liem and Scheraga, *Arch. Biochem. Biophys.* 160:133 (1974); Hageman and Scheraga, *Arch. Biochem. Biophys.* 164:707 (1974)).

A cognate function-forming element complementary to a particular CDFE comprises a complex of the molecule that is acted on by the CDFE (for example, a substrate component), transiently associated with one or more cell surface molecules or with a cellular or noncellular component of a tissue. The transient association of the molecule (substrate) with a cell surface, for example, a vascular luminal surface, results in the formation of a complement of exosites (function-forming context) that associate with the exosite recognition sites on the cognate CDFE, thereby allowing the CDFE to transiently associate with the function-forming context and effect its activity (for example, enzymatic activity on a substrate component of the function-forming context). The CDFE then is released due to the loss of one or more exosites in the complex comprising the modified substrate, and can diffuse to interact with another function-forming context.

Importantly, a CDFE has a substantially lower energy of association for the free molecule (substrate) as compared to the substrate associated with the cell surface because the free substrate exhibits fewer than all of the exosites exhibited by the surface associated substrate and the cell surface molecules to which it is associated. Similarly, the substructure with thrombogenic potential component of a CDFE, alone, does not substantially associate with the molecule, regardless of whether the molecule is free in solution or is associated with the cell surface. A CDFE is exemplified herein using a truncated tissue factor (tTF; "substructure with thrombogenic potential") operably linked to a peptide portion of kringle 5 ("selective recognition domain"), and a function-forming context recognized by the CDFE is exemplified by the transient complex formed by the association of the blood coagulation protein, factor X, and one or more specific cell surface molecules.

An interaction of a CDFE and function-forming context is illustrated in FIG. 1. By way of example, the CDFE (shown on the left of FIG. 1) comprises a modified TF ("E") operably linked to a plasminogen kringle 5 peptide (hatched region; see, also, Example I), and the function-forming context (shown on the right of FIG. 1) comprises blood coagulation factor X ("S") transiently associated with a vascular cell surface associated molecule ("SAM"). The CDFE forms a complex with activated blood coagulation factor VIIa ("VIIa"), thereby forming a CDFE:VIIa complex having enzymatic potential for factor X or factor IX as a substrate.

As shown in FIG. 1, the CDFE:VIIa complex presents four exosite recognition sites (E1 to E4), which are contributed by various portions of the CDFE:VIIa complex and are unique to the complex. Similarly, the function-forming context presents four exosites —S1 and S2, contributed by the factor X ("S"), "Exocyte" contributed by the SAM, and "N" formed by the transient interaction of S and SAM. An interaction of the exosite recognition domains of the CDFE-:VIIa complex with the exosites formed by the transient S:SAM complex provides sufficient energy of association such that the CDFE:VIIa complex has enzymatic activity for factor X (or factor IX) and cleaves factor X at the proper scissile bond, i.e., cleavage site ("ST"), to produce factor Xa (or factor IXa). The formation of the product, factor Xa, results, for example, in a conformational change in the substrate, such that S1 and S2 have lower, if any, ability to associate with E1 and E2. As a result, the CDFE:VIIa complex is released from the product and is free to interact with another S:SAM complex.

A CDFE:VIIa complex also can interact with free factor X or factor IX ("S"). However, in comparison with the four exosites presented by the S:SAM complex (see FIG. 1, right), the free factor X (or factor IX) lacks the "N" and "Exocyte" exosites. As a result, the energy of association of the CDFE:VIIa complex with free factor X or factor IX is substantially less than the energy of association of the CDFE:VIIa complex with a S:SAM complex, and is insufficient for the CDFE:VIIa complex to effect its catalytic activity. Thus, a CDFE only exhibits its functional activity when it interacts fully with the exosites of a function-forming context.

The blood coagulation cascade provides hemostasis, an essential survival function for all organisms with a circulatory system. In vertebrates, the cascade proceeds as a series of proteolytic events, starting with a cell surface receptor cofactor and culminating in the generation of thrombin, an enzyme that converts plasma fibrinogen to the stable fibrin gel. Thrombin also stimulates cells via the thrombin receptor, and platelets are activated and, in the arterial circulation, participate in formation of a thrombus that can locally occlude blood vessels. The vessel blockage results in local ischemia and causes a complex series of derivative tissue responses that result in infarctive death of tissue. When occurring outside the lumen of blood vessels, the coagulation cascade with platelets provides the necessary barrier to continued bleeding from trauma or other disruption of vascular integrity.

The integral transmembrane protein receptor tissue factor (TF) is a structural member of the cytokine receptor superfamily of cell surface receptors and the trigger that cells use to initiate the coagulation cascade on their surface. When TF comes in contact with plasma, it very rapidly binds factor VII or factor VIIa, the activated species of factor VII, to form an active and highly specific bimolecular serine protease complex, TF:VIIa, on the cell surface.

Binding of factor VIIa to TF enhances the enzymatic activation of substrate factors IX and X as much as 5,000 fold (Rao et al., *Proc. Natl. Acad. Sci., USA* 85:6687 (1988)). This complex is preferentially localized to anionic phospholipid microdomains of the surface of a thrombogenic cell of the blood or vasculature, where it cleaves a single peptidyl bond of factor X to form factor Xa, another serine protease in the blood coagulation cascade. The association of both the TF:VIIa complex and factor X with a cell provides the appropriate localization and orientation for enzymatic activity. In comparison, a tTF, which lacks the transmembrane domain and, therefore, does not associate with a cell surface, has only about 1/100,000 the activity of TF (Ruf et al, *J. Biol. Chem.* 266:2158–2166 (1991a); Ruf et al, *J. Biol. Chem.* 266:15719–15725 (1991b)).

The complex of anionic surface microdomains and factor Xa ($K_d$~100 nM) binds to its cofactor, factor Va, to form the potent prothrombinase complex, which catalyzes the conversion of prothrombin to thrombin. Factor IXa that is formed generates more factor Xa following its binding to its cofactor factor VIIIa (hemophiliac factor). This factor Xa also generates more prothrombinase complex, thrombin, cell activation, and formation of a thrombus. Several inhibitors balance and control this cascade. Factor IX is an alternative substrate for TF:VIIa in the blood coagulation factor and, like the factor X zymogen, associates with anionic membrane microdomains on a cell surface.

A CDFE is constructed such that the substructure with thrombogenic potential is positioned in the appropriate orientation to effect its activity on a molecule comprising a function-forming context. For example, a CDFE comprising tTF operably linked to a selective recognition domain positions the TF catalytic domain, in the form of a CDFE:VIIa complex, at a biologically susceptible site approximately 80 to 92 Angstroms above the surface of a cell, which is the position of the factor X cleavage site when factor X is transiently associated with a cell surface. As such, a CDFE-:VIIa complex converts cell associated factor X to Xa, but does not substantially cleave free factor X in plasma.

An approach used in the therapy of solid tumors has been to employ high affinity immunoconjugates that target the endothelium and induce coagulation the vasculature of solid tumors (Huang et al., *Science* 275:547–550 (1997)). However, there are a number of limitations associated with such a therapy, particularly the need for antibodies that are specific only for the target antigen, which must be expressed only on the target tissue. The monoclonal antibody, Herceptin® (Genentech; U.S. Pat. No. 5,772,997), which is a humanized murine antibody directed against the HER-2 receptor, has found use in treating certain cancers that over-express Her-2. Overexpression of HER-2 by tumor cells is a prognostic indicator that predicts poor clinical outcome in breast cancer and other cancers. Herceptin® inhibits growth of xenografts that over express HER-2, but not of xenografts that express normal amounts of HER-2. In addition, when Herceptin® was combined with thiotepa, an analogue of cis-platinum, and VP-16 etoposide topoisomerase II inhibitor treatment, synergistic inhibition of SK-BR-3 human breast cancer cell growth was observed in vitro. Unfortunately, Her-2 over-expression is limited to a small number of cancers and, therefore, there is only a limited opportunity to take advantage of the synergistic effect produced by Herceptin® and certain other chemotherapeutic agents. As disclosed herein, administration of a CDFE with a chemotherapeutic agent enhanced the efficacy of the chemotherapeutic agent (Example II). In particular, the combined therapy enhances the efficacy of the chemotherapeutic agent, similar to the effect obtained using a combination of HERCEPTIN and doxorubicin. However, the results disclosed herein indicate that the methods and compositions of the invention can have a broader applicability than HERCEPTIN, which is useful only in treating tumors that express high levels of HER-2/neu.

As disclosed herein, a CDFE (NV144), when administered in combination with a chemotherapeutic agent to tumor bearing animals, enhanced the efficacy of the agent by producing a significantly greater therapeutic effect on the tumors than the therapeutic effect produced by administration of the agent alone (Example II); administration of NV144 alone had little or no effect on the tumors. As such, the present invention provides methods of enhancing the efficacy of one or more agents in a subject by administering a CDFE with the agent or agents to the subject.

A CDFE useful in a composition or method of the invention contains a substructure with thrombogenic potential operably linked to a selective recognition domain. As used herein, the term "substructure with thrombogenic potential" means at least a portion of a molecule that has the ability to initiate, stimulate, promote, facilitate, propagate or otherwise affect thrombosis. The molecule can be a peptide, including an oligopeptide, polypeptide or protein, which can contain one or more modifying groups such as a glycosyl, lipidyl, or other modifying group; or can be a small organic molecule that has thrombogenic potential such as a peptidomimetic or other mimic, for example, of a protein domain having thrombogenic potential. Although a substructure with thrombogenic potential can have thrombogenic activity and, therefore, induce thrombosis, it need not exhibit the thrombogenic activity for purposes of the present invention.

A substructure with thrombogenic potential can be a coagulation factor such as tissue factor (TF), including, for example a vertebrate TF such as a human or other mammalian TF, or a modified form of a TF. A modified TF can be a TF having one or a few amino acid deletions, insertions or substitutions (see, for example, U.S. Pat. No. 5,877,289 and PCT/US98/27498), provided that the modified TF has thrombogenic potential. A modified TF is exemplified herein by a truncated TF (tTF) including amino acids 35 to 243 of human TF (see SEQ ID NO: 1 in PCT/US98/27498). Additional modified forms of a TF useful in a CDFE include any form of TF lacking portions of the transmembrane anchor region (for example, lacking amino acids 220 to 242, or amino acids 252 to 274 of SEQ ID NO: 1 in PCT/US98/27498). The TF can comprise substantially the amino terminal amino acids, for example, amino acid residue 1 to about residue 252 (SEQ ID NO: 1 in PCT/US98/27498). Such a modified TF can be further modified, for example, by substituting an amino acid residue at one or more positions such as by substituting the amino acid residue at position 167 or position 199, or a residue within 15 Angstroms of amino acid 167 or 199 (see SEQ ID NO: 1 in PCT/US98/27498) with a basic amino acid such as lysine, arginine, histidine or the like.

A substructure with thrombogenic potential also can be a coagulation factor other than TF. Coagulation factors are well known in the art and include those involved in the normal blood clotting pathway, for example, fibrinogen, prothrombin, factor V or factors VII through XIII, von Willebrand factor, tissue plasminogen activator, or other coagulation factors such as streptokinase, staphylokinase, urokinase, factor C, Mac-1, EPR-1, a venom derived coagulation enzyme such as Russell's viper venom (Kisiel, *J. Biol. Chem.* 254:12230–12234 (1979); DiScipio et al., *Biochemistry* 16:5253–5260 (1977)) or a cellular enzyme such as a granzyme (see, also, U.S. Pat. No. 5,877,289). For use in a CDFE, the substructure with thrombogenic potential can have protease activity, for example, a factors VIIIa:IXa complex, or a factors Va:Xa complex; or can be in an inactive zymogen form that can be activated to have protease or thrombogenic activity.

Although a substructure with thrombogenic potential need not have actual thrombogenic activity, a molecule useful as such a substructure can be identified using an assay that detects an activity associated with thrombogenic activity, including the amidolytic activity assay and factor X activation assay disclosed in Example I, or any of various in vitro or in vivo assays known in the art. For example, the tTF used in the exemplified CDFE (designated "NV144") can associate with factor VII to form an active NV144:VIIa complex that can cleave factor X, which is in the blood coagulation pathway and, therefore, is considered a substructure with thrombogenic potential. Similarly, factor X can be useful as a substructure with thrombogenic potential, since factor X can be activated to factor Xa, which has activity in the blood coagulation pathway. A substructure with thrombogenic potential also can be thrombin, or a peptide portion of thrombin that can cleave fibrinogen to fibrin, since such a molecule has an activity associated with the blood coagulation pathway. As such, a substructure with thrombogenic potential readily can be identified by determining that it has an ability to activate or substitute for a protein in the blood coagulation pathway.

In some cases, a molecule that affects vascular permeability can be used in place of a substructure with thrombogenic potential in a CDFE useful for enhancing the efficacy of an agent in subject. Thus, a CDFE can comprise a modified substance P peptide can be operably linked to a selective recognition domain. Substance P can increase vascular permeability in selected tissues, including trachea, esophagus and urinary bladder, and, when administered with liposome encapsulated drugs, increased the amount of the drugs in tissues that express substance P receptors in postcapillary venules, but not in other tissues (Rosenecker et al., *Proc. Natl. Acad. Sci., USA* 93:7236–7241 (1996)). By incorporating a modified substance P into a CDFE with a substructure with thrombogenic potential, a CDFE having greater and more selective specificity than substance P, alone, can be obtained.

A CDFE also contains a selective recognition domain. As used herein the term "selective recognition domain" means a molecule that, when part of a chimeric CDFE, facilitates the proper association of the CDFE to a function-forming context. A selective recognition domain contributes to the specificity and selectivity of a CDFE by associating with one or more exosites of a function-forming context, thereby facilitating the ability of the "substructure with thrombogenic potential" component of a CDFE to effect its activity and to enhance the efficacy of an agent administered with the CDFE to a subject. Generally, a selective recognition domain contributes to the optimal spatial orientation and energy of association of a CDFE for a function-forming context by at least about one order of magnitude, and usually at least about two orders of magnitude, or three orders of magnitude or more, as compared to the efficiency of orientation and energy of association of either the substructure with thrombogenic potential alone or the selective binding domain alone for the function-forming context or an individual component of the function-forming context; Thus, a selective recognition domain contributes one or more exosite recognition sites to a CDFE, thereby contributing energy of association to the CDFE, including, for example, proper rotational orientation and proper distance of a catalytic site of the CDFE with, for example, a cleavage site of a molecule transiently associated with a cell surface (i.e., a complex providing an appropriate function-forming context).

The term "exosite" is used herein to mean a three dimensional conformation of a molecule or complex of molecules that is recognized by and can interact with a cognate site ("exosite recognition site") on a second molecule or complex of molecules. With respect to the present invention, a CDFE presents a macromolecular surface having one or more exosite recognition sites that interact with complementary exosites present on a cognate function-forming context, thus allowing a selective association of the CDFE and the function-forming context. One or more exosite recognition sites exhibited by a CDFE is contributed by the selective recognition domain, or is formed due to a three dimensional structure that is formed by the CDFE, but not by either the substructure with thrombogenic potential or the selective recognition domain, which comprise the CDFE, alone. Similarly, the complementary exosites presented by the function-forming context are formed, at least in part, due to the transient association of a particular molecule with a cell surface or a cellular or noncellular component of a tissue and, therefore, are unique to the complex. The interaction of exosite recognition sites presented by a CDFE with the exosites presented by a function-forming context is analogous to the classical "lock and key" interaction formed between an enzyme and its substrate, but is distinguishable, in part, because the "substrate" (function-forming context) for a CDFE exists only transiently. Modular components useful as selective recognition domains contributing exosite recognition sites to a CDFE can be identified as disclosed herein or otherwise known in the art (see, for example, Parry et al., *Biochem.* 290:665–670 (1993); Wu et al., *J. Biol. Chem.* 267:24408–24412 (1992); Rogers et al., *J. Biol. Chem.* 267:3613–3617 (1992)).

As used herein, the term "function-forming context" refers to the transient conformational state that occurs due to the specific association of a first molecule, which is not stably associated with a selected cell or tissue in a subject, with a second molecule that is expressed on the surface of the selected cell or on a cellular or noncellular component of the selected tissue. A function-forming context reveals a biologically susceptible site, which can be acted upon by a CDFE, for example, a cleavage site that can be cleaved by a CDFE having enzymatic potential. For convenience of discussion, the term "function-forming context" also is used to refer to the transient complex formed by the association of a particular molecule with a particular component of a cell surface or tissue. A function-forming context can occur due, for example, to the transient association of a plasma protein to anionic phospholipid microdomains present on a vascular surface, wherein the transient interaction results in the presentation of one or more exosites that are unique to the complex and recognized and bound by the exosite recognition sites on a cognate CDFE. As disclosed herein, a CDFE associates more efficiently with such a transiently bound plasma protein than to the free plasma protein or to the anionic phospholipid microdomains or other participating cell surface molecules, such that a potential activity of the CDFE can be effected.

A selective recognition domain can be formed by one or more peptides, including an oligopeptide, polypeptide, or protein, which may or may not be modified with a glycosyl, lipidyl or other group, for example, a group that can be added by post-translational modification to a peptide in a cell or by chemical modification of a peptide. The selective recognition domain also can be a small organic molecule such as a peptidomimetic or other molecule that facilitates the selective association of a CDFE with a function-forming context. In addition, a selective recognition domain can be a nucleic acid molecule, which can contribute an exosite to facilitate the association of a CDFE to a function-forming context. Methods of making and identifying nucleic acid molecules that have specific binding activity for a peptide or other molecule are well known (see, for example, O'Connell et al., *Proc. Natl. Acad. Sci., USA* 93:5883–5887 (1996); Tuerk and Gold, *Science* 249:505–510 (1990); Gold et al., *Ann. Rev. Biochem.* 64:763–797 (1995)) Although no mechanism is proposed herein, specific association of a CDFE with a function-forming context can occur, in part, due to cooperative effects of the exosite recognition sites presented by the CDFE with the exosites presented by the function-forming context. As a result, the energy of association of the CDFE and the function-forming context is substantially greater than that of any single component of the CDFE with the function-forming context, or any single component of the function-forming context alone with the CDFE.

A selective recognition domain is exemplified by a kringle domain, for example, a kringle 5 domain, or a peptide portion thereof such as the amino acid sequence Pro-Arg-Lys-Leu-Tyr-Asp (SEQ ID NO: 1; see U.S. Pat. No. 5,801, 146; *Biochemistry* 30(7): 1948–1957 (1991)). As such, the present invention also provides a peptide having the amino acid sequence set forth as SEQ ID NO: 1, as well as chimeric molecules, for example, fusion polypeptides, that contain SEQ ID NO: 1. Such fusion polypeptides can include SEQ ID NO: 1 and an amino acid sequence of any polypeptide that is heterologous with respect to plasminogen. Specifically excluded from a composition of the invention is a plasminogen polypeptide, which contains SEQ ID NO: 1, or any peptide portion of plasminogen that contains SEQ ID NO: 1 (see U.S. Pat. No. 5,801,146).

Kringle domains, which are present in several proteins, contain about eighty amino acids that are rigidly constrained by six highly conserved cysteine residues that form three disulfides in an intertwined 1–6, 2–4, and 3–5 pattern. The kringle domains in plasminogen bind other plasma proteins, cells, cell-associated proteins, and fibrin clots, and such binding appears to depend on specific lysine residues in the kringle domain. Angiostatin, which contains kringle domains 1, 2 and 3 of plasminogen, inhibits angiogenesis apparently by inhibiting endothelial cell growth (*Cell* 79(2) :315–328 (1994)). Kringle 5, which is not part of angiostatin, also inhibits endothelial cell growth, and is a selective inhibitor for endothelial cell migration (IC50=500 nM). Kringle 5 of plasminogen can bind lysine, or lysine analogs such as ε-aminocaproic acid (26 μM), 5-aminopentanoic acid (580 μM), and 7-aminoheptanoic acid (367 μM; Chang et al., *Biochemistry* 37:3258 (1998)). As disclosed herein, single or multiple kringle domains such as kringle 1, kringle 2 or the like from plasminogen; or angiostatin; or fragments thereof can be used as a selective recognition domain.

Additional selective recognition domains useful in constructing a CDFE include cell surface recognition domains, including, for example, annexin domains; charged phospholipid associating elements; protease inhibitors; peptide sequences or small organic molecules that facilitate orientation by recognizing molecules or molecular assemblies enriched in tumor vasculature endothelium, for example, growth factors, ligands, hormones, or lectins, which have transient functional association properties, and the like. A selective recognition domain also is exemplified herein by the urokinase plasminogen activator receptor (uPAR) binding antagonist peptide referred to as clone 20 (SEQ ID NO: 2; see Goodson et al., *Proc. Natl. Acad. Sci., USA* 91:7129–7133 (1994); see, also, NuV124, SEQ ID NO: 24 in Example 6 of PCT/US98/27498), or can be prepared from other uPAR antagonists, anti-angiogenic proteins such as endostatin from the collagen XVIII 20 kiloDalton carboxy terminus, (O'Reilly et al., *Cell* 88:277–285 (1997)); nucleotide sequences 1502 to 2053 from genbank HUMCOL18AX ACCESSION L22548); peptides derived from thrombospondin-1 (TSP-1), for example, TSP-1 Mal III (*J. Cell Biol.* 122:497–511 (1993)); peptide 246 (*Proc. Natl. Acad. Sci., USA* 89:3040–3044 (1992)); laminin binding peptides such as Peptide G (Guo et al, *J. Biol. Chem.* 267:17743–17747 (1992)); proliferin (*J. Biol. Chem.* 263(7) :3521–3527 (1988)); proliferin-related peptide (*Mol. Endocrinol.* 2(6):579–586 (1988)); membrane binding peptide from factor VIII (*Biochemistry* 34(9):3022–3031 (1995)); phosphatidyl-serine binding proteins such as annexin V (*J. Biol. Chem.* 270:21594–21599(1995)), or the like.

A selective recognition domain useful for preparing a CDFE also can be identified by screening a combinatorial library including, for example, a phage display library of peptides, which can be constrained peptides (see, for example, U.S. Pat. No. 5,622,699; U.S. Pat. No. 5,206,347; Scott and Smith, *Science* 249:386–390 (1992); Markland et al., *Gene* 109:13–19(1991)); a peptide library (U.S. Pat. No. 5,264,563); peptidomimetic libraries (Blondelle et al., supra, 1995); a nucleic acid library. (O'Connell et al., supra, 1996; Tuerk and Gold, supra, 1990; Gold et al., supra, 1995); an oligosaccharide library (York et al., *Carb. Res.*, 285:99–128, (1996); Liang et al., *Science*, 274:1520–1522, (1996); and Ding et al., *Adv. Expt. Med. Biol.*, 376:261–269, (1995)); a lipoprotein library (de Kruif et al., *FEBS Lett.*, 399:232–236, (1996)); a glycoprotein or glycolipid library (Karaoglu et al., *J. Cell Biol.*, 130:567–577 (1995)); or a chemical library containing, for example, drugs or other pharmaceutical agents (Gordon et al.,*J. Med. Chem.*, 37:1385–1401 (1994); Ecker and Crooke, *Bio/Technology*, 13:351–360 (1995)). A molecule useful as a selective recognition domain can be identified by examining it for the ability to facilitate functionally effective association of a substructure with thrombogenic potential to a function-forming context. For example, a molecule useful as a selective recognition domain can be identified by substituting the kringle 5 peptide in NV144 (see Example I) with the molecule, and examining the substituted "CDFE" for the ability to form a complex with factor VIIa and cleave factor X (or factor IX) in a function-forming context to Xa (or IXa). Where such facilitated cleaving activity is identified, the amount of cleavage can be compared with that produced by NV144 or with that produced by tTF alone, and a molecule that facilitates the activity of the substructure with thromobogenic potential can be selected.

A CDFE can have an enzymatic activity such as the serine protease activity exhibited by various blood coagulation factors. A CDFE that enhances the efficacy of an agent in a subject is exemplified herein by a truncated TF operably linked to peptide portion of a plasminogen kringle 5 domain (NV144), and the function-forming context is formed due to transient association of factor X with one or more specific molecules on a vascular surface. When administered to a subject, NV144 forms a complex with activated factor VIIa (NV144:VIIa), which can productively associate transiently at the function-forming context formed by the association of factor X with the particular cell surface molecules. The NV144: VIIa complex associates more productively with the function-forming context than do any elements of the complex, alone. Similarly, the NV144:VIIa complex associates less productively with the vascular surface molecules, absent factor X, or with factor X when it is not associated with the particular vascular surface. Such specific association of the CDFE depends on the transient association of factor X with a vascular cell surface or a cellular or noncellular component of vascular tissue to produce a function-forming context. As suggested above, the increased susceptibility of a substrate component of a function-forming context, as compared to the susceptibility of the substrate component alone, may be due, for example, at least in part to an increased energy of association contributed by interactions of the unique exosite recognition sites that are exhibited by the CDFE and the unique exosites presented by the function-forming context.

A CDFE comprises a substructure with thrombogenic potential operably linked to one or more selective recognition domains. As used herein, the term "operably linked" means that the substructure with thrombogenic potential is bound to a selective recognition domain such that the CDFE, when associated with a function-forming context, exhibits the function for which it was constructed. Since a CDFE generally is used to enhance the efficacy of one or more agents in vivo, ex vivo or in vitro, the means for operably linking the modular components of a CDFE is stable for the particular conditions to which the CDFE is exposed. Thus, where the CDFE is administered to a subject, the modular components are operably linked such that they remain bound under the particular physiological conditions to which the CDFE is exposed, for example, in various portions of the alimentary tract, in the circulation, in the cerebrospinal fluid, or the like.

A substructure with thrombogenic potential can be bound to a selective recognition domain directly or indirectly through a spacer element. For example, where the substructure with thrombogenic potential and the selective recognition domain comprising the CDFE are peptides, the two elements can be operably linked directly by a peptide bond between the carboxy terminus of one peptide and amino terminus of the other; by a di-tryptophan crosslink between a Trp residue in each peptide; by a disulfide crosslink between two Cys residues; by a lactam crosslink formed by a transamidation reaction between the side chains of an acidic amino acid in one peptide and a basic amino acid in the other, such as between the y carboxyl group of Glu and the ε-arnino group of Lys; by a lactone crosslink formed between the hydroxy group of Ser and the γ-carboxyl group of Glu; or by any other covalent bond formed between an amino acid in each peptide, one or both of which can have a modified side chain. A substructure with thrombogenic potential also can be operably linked to a selective recognition domain through a noncovalent bond such as through a hydrophilic or hydrophobic association, for example, through a leucine zipper, provided the noncovalent interaction is stable under the particular conditions to which the CDFE will be exposed.

A substructure with thrombogenic potential and a selective recognition domain also can be crosslinked using N-hydroxysuccinimide (NHS)-ester haloacetyl crosslinkers, photoreactive crosslinkers, and the like (see, for example, Pierce Chemical Co. catalogue; Wong, "Chemistry of Protein Conjugation and Crosslinking" (CRC Press, 1991); Hermanson, "Bioconjugate Techniques" (Academic Press 1995)). Crosslinking agents generally react with a functional group present on each of the peptides to be crosslinked, and include homobifunctional and heterobifunctional reagents such as N-succinimidyl(4-iodoacetyl) aminobenzoate, dimaleimide, dithio-bis-nitrobenzoic acid, N-succinimidyl-S-acetyl-thioacetate, N-succinimidyl-3-(2-pyridyldithio) propionate, succinimidyl 4-(N-maleimidomethyl) cyclohexane-1-carboxylate, and 6-hydrazinonicotimide. If desired, the crosslinking agent can be selected based on its ability to form a selectively cleavable bond, for example, a photolabile crosslink formed using 3-amino-(2-nitrophenyl) propionic acid (Rothschild et al., *Nucleic Acids Res.* 24:351–66 (1996)). A substructure with thrombogenic potential also can be modified, for example, to contain a biotin group, which can bind to a selective recognition domain that has been modified to contain an avidin group.

A substructure with thrombogenic potential and a selective recognition domain also can be operably linked through a spacer element. A spacer element is selected, for example, based on the requirement that the exosite recognition site formed by the substructure with thrombogenic potential and the selective recognition domain are properly positioned and oriented for recognition and interaction with exosites on a particular function-forming context. For example, a spacer element having the amino acid sequence $(Gly_4Ser)_3$ (SEQ ID NO: 3) was used to operably link the tTF polypeptide with the kringle 5 peptide. Such a spacer element has desirable characteristics, including, for example, rotational flexibility, which facilitates proper orientation of the CDFE exosite recognition sites upon encountering the exosites exhibited by a cognate function-forming context. Such a spacer element also can be used with a selective recognition domain comprising the entire about 80 amino acid kringle 5 domain, but may not be required if, for example, the additional sequence of the kringle 5 domain allows for proper orientation of the exosite recognition sites. The selection of a spacer element can be based, for example, on crystallographic data, where available, such that a spacer having an appropriate length, rotational ability, or other relevant conformational contribution is selected, or can be determined empirically using methods as disclosed herein for determining the functional efficiency of a CDFE for a function-forming context, for example, by substituting the spacer element of NV144 with a molecule to be examined as a potential spacer element.

A spacer element can be a peptide, a peptidomimetic, or a small organic molecule, and can comprise homobifunctional or heterobifunctional crosslinking agents or chitin oligomers. A spacer element can include combinations of Gly and Ser residues such as $((Gly)_4Ser)_n$ (SEQ ID NO: 4), $((Ser)_4Gly)_n$ (SEQ ID NO: 5), and the like, where "n" is about 1 to about 20, generally about 2 to about 15, and particularly about 3 to about 10, or can be a peptide based on the hinge region of the heavy chain of immunoglobulin (Ig) proteins, for example, a heavy chain IgD sequence. (see Kabat et al., "Sequences of Proteins of Immunological Interest" 5th Ed. (U.S. Dept. of Human Health Services)). The cysteine residues in a hinge region can be substituted by a glycine, alanine, or serine residue, in any combination, to minimize the likelihood of a cysteine thiol group disrupting the spacer structure or inhibiting proper formation of the CDFE. Generally, a peptide spacer element is non-immunogenic, and is about 2 to about 100 amino acids in length, generally about 6 to 75 amino acids in length, usually about 10 to 40 amino acids in length, and particularly about 15 to 30 amino acids in length.

Where the components of a CDFE, including a substructure with thrombogenic potential, a spacer element, and a selective recognition domain are prepared or otherwise obtained as separate entities, the components can be linked using chemical or photoreactive methods as disclosed herein or otherwise known in the art. In particular, reactive groups and reaction conditions for linking the components are selected such that an operable CDFE is obtained. For example, where it is desired that a CDFE comprises, in order from the amino terminus to the carboxy terminus, the selective recognition domain, the spacer element, and the substructure with thrombogenic potential, the selective recognition domain can be modified at its carboxy terminus to contain, for example, a biotin molecule; the spacer element can be modified at its amino terminus to contain an avidin molecule, and at its carboxy terminus to contain a photoreactive group; and the substructure with thrombogenic potential can be modified at its amino terminus to contain a cognate photoreactive group that forms a crosslink with the group on the spacer element. Upon performing the appropriate reactions, a CDFE having the desired structure is obtained.

The choice of a spacer element will depend, in part, on the method selected for preparing the CDFE, which can be, for example, by chemical synthesis of the CDFE or an element thereof, by purification of one or more elements of the CDFE, or by synthesis of the CDFE or a component thereof using recombinant DNA methods. A synthetic polypeptide substructure with thrombogenic potential or selective recognition domain can be produced, for example, by chemical methods of peptide synthesis using an Applied Biosystems, Inc., Model 430A or 431A automatic polypeptide synthesizer and chemistry provided by the manufacturer. Alternatively, an element of a CDFE such as TF can be isolated, for example, from cells expressing the substructure with thrombogenic potential, including from cells that have been transformed or transfected with an expression vector comprising a nucleotide sequence encoding TF or a modified TF (see, for example, PCT/US98/27498; U.S. Pat. No. 5,877,289). Various coagulation factors or other peptides useful in preparing a CDFE can be obtained using methods known in the art, or can be purchased from commercial sources, Factor VII, for example, can be prepared as described by Fair (1983) Blood 62:784–791, and recombinant factor VIIa can be purchased from Novo Biolabs (Danbury, Conn.).

A CDFE, or an element thereof, conveniently can be prepared using recombinant DNA methods (see, for example, Ausubel et al., "Current Protocols in Molecular Biology" (Greene Publishing Associates, Inc., and John Wiley & Sons, Inc. (1993)); Sambrook et al., "Molecular Cloning: A laboratory manual" (Cold Spring Harbor Laboratory Press 1989). For example, a nucleotide sequence encoding a substructure with thrombogenic potential can be linked (or synthesized) in frame with a sequence encoding a selective recognition domain, and, if desired, a sequence encoding a spacer element can be linked in frame between the two nucleotide sequences. The nucleic acid molecule can be cloned into an expression vector and expressed in a suitable host cell. Expression vectors and suitable host cells, including, for example, bacterial systems such as $E.\ coli$; yeast systems such as Saccharomyces or Pichia; insect systems such as Baculovirus; and mammalian cell systems such as NIH3T3 cells, Cos cells, 293 cells, and the like, are well known in the art and can be obtained from the American Type Culture Collection or purchased from commercial sources (for example, Promega Corp., Madison Wis.; Invitrogen, La Jolla Calif.).

A CDFE, or a component thereof, can be encoded by a recombinant nucleic acid molecule and expressed in a cell. Preparation of a CDFE by recombinant methods provides several advantages. In particular, the nucleic acid sequence encoding the CDFE can include additional nucleotide sequences encoding, for example, peptides useful for obtaining the CDFE in a purified form. As used herein, the term "purified" means that the molecule is substantially free of contaminants normally associated with a native or natural environment. A CDFE can be purified using well known methods, including, for example, precipitation, gel filtration, ion exchange, reversed-phase, or affinity chromatography (see, for example, Deutscher et al., "Guide to Protein Purification" in *Meth. Enzymol.*, Vol. 182, (Academic Press, 1990)). Such methods also can be used to purify a component of a CDFE, for example, a substructure with thrombogenic potential, from a cell in which it is naturally expressed.

A recombinant nucleic acid molecule encoding a CDFE or a component thereof can include, for example, a protease site, which can facilitate cleavage of the CDFE from a non-CDFE sequence, for example, a tag peptide, secretory peptide, or the like. As such, the recombinant nucleic acid molecule also can encode a tag peptide such as a polyhistidine sequence, a FLAG peptide (Hopp et al., *Biotechnology* 6:1204 (1988)), a glutathione S-transferase polypeptide or the like, which can be bound by divalent metal ions, a specific antibody (U.S. Pat. No. 5,011,912), or glutathione, respectively, thus facilitating purification of the CDFE comprising the peptide tag. Such tag peptides also can facilitate identification of the CDFE through stages of synthesis, chemical or enzymatic modification, linkage, or the like. Methods for purifying polypeptides comprising such tags are well known in the art and the reagents for performing such methods are commercially available.

A nucleic acid molecule encoding a CDFE can be engineered to contain one or more restriction endonuclease recognition and cleavage sites, which can facilitate, for example, substitution of an element of the CDFE such as the selective recognition domain or, where present, a spacer element. As such, different but related CDFEs can be prepared, each having a similar activity, but having specificity for different function-forming contexts. A restriction endonuclease site also can be engineered into (or out of) the sequence coding a peptide portion of the CDFE, and can, but need not change one or more amino acids encoded by the particular sequence. Such a site can provide a simple means to identify the nucleic acid sequence, based on cleavage (or lack of cleavage) following contact with the relevant restriction endonuclease, and, where introduction of the site changes an amino acid, can further provide advantages based on the substitution. For example, a specific amino acid residue such as a threonine can be introduced at position 212 or position 245 of TF (see SEQ ID NO: 1 in PCT/US98/27498) to yield a restriction site favorable to splicing with the sequence encoding the modified TF with a nucleotide sequence encoding a spacer element or selective recognition domain (see, for example, U.S. Pat. No. 5,877,289).

A CDFE interacts with a function-forming context occurring selectively on the surface of a particular cell or on a cellular or noncellular component of a tissue in a subject, for example, on certain vascular tissues such as tumor associated vascular tissue, thereby enhancing the efficacy of the agent at the site of the cell or tissue. The cell can be an endothelial cell, a cell present in the circulation, for example, a cell involved in thrombogenesis, or a cell present in a particular tissue, including, for example, a tumor cell, a fibroblast, a chondrocyte, an osteocyte, or a cell derived from the bone marrow such as a histiocyte. A noncellular component associated with a tissue can be a matrix material such as collagen, elastin, fibronectin, or other component of a basement membrane or other subendothelial layer of a blood vessel, or the like.

A method of the invention can be performed by administering a CDFE and one or more agents to a subject. The agents can be diagnostic agents, nutritional molecules, toxins, therapeutic agents, radiomodulating agents, or combinations thereof. For example, a method of the invention can be performed by administering a CDFE and one or more therapeutic agents such as a combination of cancer chemotherapeutic agents used to treat a particular type of cancer. In addition, the agent, or one or all of a combination of agents, can be contained in an encapsulating medium such as a liposome, which can be a modified liposome such a stealth liposome or other "masked" liposome.

A method of the invention can be performed using a diagnostic agent, which is detectable external to the subject, thus providing a means for performing in vivo diagnostic imaging, for example, to identify the presence of a cancer in a subject. For such a method, a diagnostic agent such as a gamma ray emitting radionuclide, for example, indium-111 or technitium-99, or gadolinium-containing liposomes, can be administered with a CDFE to a subject, and can be detected using a solid scintillation detector. Similarly, a positron emitting radionuclide such as carbon-11 or a paramagnetic spin label such as carbon-13 can be coadministered with a CDFE and can be detected using positron emission transaxial tomography or magnetic resonance imaging, respectively. Such methods can identify a primary tumor as well as a metastatic lesion, which may not be detectable using other methods, and can detect other pathologic conditions having a vascular component.

The effect of a CDFE on blood vessels can be monitored, for example, by intravital microscopy in a dorsal skinfold chamber (Torres Filho et al., *Microvasc. Res.* 49:212–226 (1995); Borgstrom et al., *The Prostate* 35:1–10 (1998); Borgstrom et al., *Cancer Res.* 56:4032–4039 (1996)). To facilitate visualization of a tumor, for example, a marker such as a nucleic acid molecule encoding green fluorescent protein can be transfected into the tumor cells under control of an inducible or a constitutive regulatory element and fluorescence can be monitored in the chamber. To facilitate monitoring of blood vessels, fluorescently labeled dextran or other such molecule, which does not readily traverse an intact vascular system, can be introduced into blood vessels and the integrity of the vasculature can be monitored in situ. Such methods can be useful to identify a CDFE that, for example, alters the permeability of the vascular system, as was observed for NV144.

Having identified the presence of a cancer or other pathologic condition in a subject, a CDFE can be administered with a cytotoxic agent such as ricin A chain or a cancer chemotherapeutic agent to the subject in order to enhance the therapeutic efficacy of the agent in the subject. A therapy modulating agent such as a chemosensitizing agent or a radiomodulating agent also can be a useful therapeutic agent where a subject is to be treated by radiotherapy. A radiomodulating agent, for example, can be a radiosensitizer, which can be administered with a particular CDFE to sensitize a tumor to the effects of radiation, or can be a radioprotector, which can be administered with a particular CDFE to protect normal tissue within a radiation field. Administration of a combination of such agents with a CDFE can be particularly useful for treating a pathologic condition. Thus, the invention provides a method of treating a pathologic condition in a subject by administering to the subject one or more therapeutic agents and a CDFE, which contains a substructure with thrombogenic potential, and a selective recognition domain, whereby interaction of the CDFE with a function-forming context on a cell or tissue in the subject enhances the efficacy of the therapeutic agent or agents in the subject, thereby treating the pathologic condition (see Example II).

A pathologic condition amenable to treatment by a method of the invention can be a cell proliferative disorder having a vascular component. For purposes of the present invention, a pathologic condition having a vascular component can be identified by the presence in a tissue of blood vessels that express cell surface markers other than those normally expressed by blood vessels in the tissue. For example, growth of a neoplasm, which can be a benign neoplasm or a malignant neoplasm, generally is characterized, at least in part, by angiogenesis. As disclosed herein, a CDFE, when administered to an experimental animal bearing a syngeneic metastatic breast carcinoma, resulted in substantial leakage from the blood vessels associated with the tumor, but not from other blood vessels, and when administered in combination with a chemotherapeutic agent, enhanced the efficacy of the agent against the tumor, but did not result in similar adverse effects by the agent against normal tissues (Example II).

Various pathologic conditions have a vascular component and, therefore, are amenable to treatment using a method of the invention. Progressive tumor growth, for example, requires angiogenesis to meet the nutritional needs of the expanding tumor mass. Numerous anatomical, morphological and behavioral differences between tumor-associated blood vessels and normal ones have been documented (see, for example, Dvorak et al., *Cancer Cells*. 3:77–85 (1991)); Jain, *Cancer Res*, 48:2641–2658 (1988)); Denekamp, *Cancer Metast Rev*. 9:267–282 (1990)). As such, a method of the invention can be useful for treating a subject having a malignant neoplasm, including a carcinoma or fibrosarcoma of the breast, prostate, lung, liver, colon, rectum, kidney, stomach, pancreas, ovary, bladder, cervix, uterus, brain, or other malignant neoplasm, including metastatic lesions. Angiogenesis also occurs in diabetic retinopathy and corneal graft neovascularization, but generally not in normal retina or cornea and, therefore, these conditions can be amenable to treatment using a method of the invention. Other pathologic conditions amenable to treatment using a method of the invention include neovascular glaucoma; benign neoplasms such as benign prostatic hyperplasia, meningioma, hemangioma and angiofibroma; inflammatory conditions, including synovitis, dermatitis and bacterial infection or other infectious condition; endometriosis; arthritis, including rheumatoid arthritis; atherosclerosis and atherosclerotic plaques; trachoma; nonunion fractures; Osler-Weber syndrome; conditions associated with vascular restenosis, arteriovenous malformations, hemophilic joints, or the formation of hypertrophic scars or of vascular adhesions; and conditions associated with granulation tissues, including burns, pyogenic granuloma, and the like. While wound healing generally is not considered a pathologic condition, it nevertheless can be facilitated using a method of the invention. For example, a CDFE having appropriate specificity can be administered in combination with an antibiotic to a subject undergoing wound healing, thereby enhancing the efficacy of the antibiotic to prevent infection at the site of the wound healing. It should be recognized that angiogenesis need not be occurring, however, for a method of the invention to produce the desired enhanced efficacy. All that is required is that a cell surface or a cellular or noncellular component of a tissue involved in the pathologic condition provides an appropriate environment such that a particular molecule can transiently associate with the surface to produce a function-forming context specific for a particular CDFE.

Where the pathologic condition to be treated is a malignant neoplastic disease, the therapeutic agent can be a cancer chemotherapeutic agent, for example, an antimetabolite, including a purine or pyrimidine analog such as 5-fluorouracil or 6-thioguanine, or a folate analog such as methotrexate, or the like; a plant alkaloid such as vincristine or paclitaxel; an alkylating agent such as cyclophosphamide or thiotepa, and including nitrosoureas and platinum compounds; an antitumor antibiotic such as doxorubicin or bleomycin; a cytokine such as interleukin-2 or transforming growth factor β; or a hormone or hormone antagonist (see, for example, "Harrison's Principles of Internal Medicine" 13th ed (eds., Isselbacher et al.; McGraw-Hill, Inc. 1994)). The skilled artisan will know that a chemotherapeutic agent is selected based, for example, on the type of neoplasm being treated, the expression of one or more markers by the tumor, and the age and general health of the subject to be treated.

The invention further provides pharmaceutical compositions, which contain an agent and a CDFE in a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition, which can include, for example, orally or parenterally such as intravenously, and by injection, intubation, or other such method known in the art.

The pharmaceutical composition also contains an agent such as a diagnostic agent, nutritional substance, toxin, or therapeutic agent, particularly a cancer chemotherapeutic agent. The agent can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981)). Liposomes, for example, which consist of phospholipids or other lipids, are nontoxic, physiologically acceptable and metabolizable carriers that are relatively simple to make and administer. "Stealth" liposomes (see, for example, U.S. Pat. Nos. 5,882,679; 5,395,619; and 5,225,212) are an example of such encapsulating materials particularly useful for preparing a composition of the invention and for practicing a method of the invention, and other "masked" liposomes similarly can be used, such liposomes extending the time that the agent or agents remain in the circulation. Approved liposomal formulations of cancer chemotherapeutic agents are available, including, for example, DOXIL (Sequus Pharmaceuticals, Inc., Menlo Park Calif.) and DaunoXome (NeXstar Pharmaceuticals, Inc., Boulder Colo.), which are liposomal formulations of doxorubicin.

The route of administration of a pharmaceutical composition of the invention will depend, in part, on the chemical structures of the CDFE and the agent. Peptides, for example, are not particularly useful when administered orally because they can be degraded in the digestive tract. However, methods for chemically modifying peptides to render them less susceptible to degradation by endogenous proteases or more absorbable through the alimentary tract are well known (see, for example, Blondelle et al., supra, 1995; Ecker and Crook, supra, 1995). In addition, suitable CDFEs can be prepared from components that are identified from libraries of peptides containing D-amino acids; peptidomimetics consisting of organic molecules that mimic the structure of a coagulation factor; or peptoids such as vinylogous peptoids, using the screening methods disclosed herein.

A pharmaceutical composition comprising a CDFE and an agent can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the pharmaceutical composition can be administered by injection, intubation, orally or topically, the latter of which can be passive, for example, by direct application of an ointment, or active, for example, using a nasalspray or inhalant, in which case one component of the composition is an appropriate propellant. A pharmaceutical composition also can be administered to the site of a pathologic condition, for example, intravenously or intra-arterially into a blood vessel supplying a tumor.

The total amount of a CDFE and the agent or agents to be administered can be administered to a subject as a single dose, either as a bolus or by infusion over a relatively short period of time, or can be administered using a fractionated treatment protocol, in which multiple doses are administered over a prolonged period of time. One skilled in the art would know that the amount of the pharmaceutical composition to treat a pathologic condition in a subject depends on many factors including the age and general health of the subject as well as the route of administration and the number of treatments to be administered. In view of these factors, the skilled artisan would adjust the particular dose as necessary. In general, the formulation of a composition of the invention and the routes and frequency of administration are determined, initially, using Phase I and Phase II clinical trials.

It should be recognized that a method of the invention does not require that the CDFE and the agent be administered as a single composition. As such, the CDFE and the agent need not be contained within a single pharmaceutical composition, but can be, for example, an oral formulation of the CDFE such as a tablet, and a solution or suspension form of the agent such as formulated in a stealth liposome. Thus, either or both the CDFE and the agent can be in admixture with an organic or inorganic carrier or excipient suitable for enteral or parenteral applications, and the CDFE or the agent can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes may be used, for example a stabilizing dry agent such as triulose (see, for example, U.S. Pat. No. 5,314,695). The CDFE and the agent are included in a pharmaceutical composition, or as separate components in a kit, in an amount sufficient to ameliorate the pathologic condition to be treated.

The following examples are intended to illustrate but not limit the invention in any manner, shape, or form, either explicitly or implicitly. While they are typical of those that might be used, other procedures, methodologies, or techniques known to those skilled in the art alternatively may be used.

EXAMPLE I

Preparation of a Context-dependent Functional Entity

This example describes the preparation and characterization of a CDFE designated NV144.

NV144 was prepared as described in Examples 11 and 12 of PCT/US98/27498. NV144 contains three elements: 1) a truncated TF domain-amino acids 3 to 211 of human TF (see SEQ ID NO: 1 in PCT/US98/27498); 2) a peptide portion of human plasminogen kringle 5 - Pro-Arg-Lys-Leu-Tyr-Asp (SEQ ID NO: 1); and 3) a spacer element-$(Gly_4Ser)_3$ (SEQ ID NO: 3). The tTF domain was engineered to bind factor VII or factor VIIa present in plasma and generate specific proteolytic function. However, the tTF domain can proteolytically activate a substrate of the thrombogenic cascade only when the substrate is precisely oriented on an appropriately activated vascular endothelial cell. The $(Gly_4Ser)_3$ spacer, which has been used in engineering single chain Fv fragment, was selected for its flexibility, presumed lack of secondary structure, and solubility. A hexahistidine tag also was included in the synthesized peptide and was used for purification purposes.

NV144 was expressed in *E. coli* cells essentially as described in PCT/US98/27498 (see Example 6). Briefly, *E. coli* cells were grown in a rich medium to a density of 1.0 to 2.0 OD units, then induced with IPTG. After an appropriate time, the cells were harvested by centrifugation and either processed (see, also, PCT/US98/27498) or stored at −80° C. For processing, *E. coli* were suspended in buffer and sonically disrupted in the presence of lysozyme. Inclusion bodies were obtained by centrifugation, and the insoluble protein was washed twice with buffer, then solubilized in 6 M guanidine HCl. NV144 was purified by nickel ion affinity chromatography (IMAC) using the hexahistidine tag. After extensive washing, imidazole was used to release the NV144 from the column.

For folding, dithiothreitol was added to a final concentration of 50 mM and the protein in 6 M guanidine was incubated overnight at room temperature to completely reduce disulfide bonds. The protein was diluted into buffer containing 0.8 M guanidine HCl (room temperature) containing a redox mixture of oxidized and reduced glutathione. The sample was centrifuged to remove insoluble material and the NV144 was concentrated by ultrafiltration. Thrombin was added to proteolytically remove the polyhistidine tag. Finally, the peptide was subjected to ion exchange chromatography using FPLC and a Pharmacia MonoQ-HR 10/10 column. A gradient elution was used to elute the protein between 20 mM TrisCl, pH 8.5, and 1 M NaCl, 20 mM TrisCl, pH 8.5.

The NV144 was determined to be greater than 95% pure by SDS-PAGE and Coomassie Blue staining. Appropriate molecular weight markers were used to determine the approximate molecular mass of the peptide. The mass of NV144 also was obtained by MALDI mass spectrometry and agreed with the theoretical mass. Endotoxin contamination was evaluated using the LAL QCL-1000 assay kit (Biowhittaker). Representative NV144 preparations contained less than 0.5 EU/ml, which is acceptable for animal testing and meets FDA standards for human use.

The ability of the NV144 to bind factor VIIa with was determined by surface plasmon resonance with a Biacore 2000 instrument, and by titrating the amidolytic activity of factor VIIa against different concentrations of the protein. NV144 exhibited affinity for factor VIIa that was comparable to the affinity of the isolated truncated TF (tTF) domain alone (see Table I).

The proteolytic activity of the NV144:VIIa complex was determined using a linked functional assay that measured the factor Xa activity that resulted from incubating NV144:VIIa with factor X. NV144 showed a normal rate of fluid phase factor Xa generation as compared to tTF (see Table I).

TABLE I

| Protein | Yield of Protein mg/liter | Kd for VIIa amidolytic activity nm | Kd for VIIa Biacore nm | Relative Proteolytic Activity |
|---|---|---|---|---|
| TF 1-218 | 50.0 | 4.73 | 3.26 | 1.00 |
| NV144 | 70.0 | 4.32 | 3.22 | 0.86 |

These results demonstrate that the TF portion of the NV144 folded properly and that binding to factor VIIa and proteolytic activity for factor X were not affected by the presence of the amino terminal peptide.

EXAMPLE II

NV144 Enhances the Efficacy of a Chemotherapeutic Agent

This example demonstrates that NV144, when administered in combination with a cancer chemotherapeutic agent, increases the efficacy of the agent in treating a cancer.

Intravital microscopy (Torres Filho et al., supra, 1995; Borgstrom et al., supra, 1996, 1998)) was used to observe the effect of NV144 on tumors and tumor vessels in a skinfold chamber. NV144 was infused over 30 min into an A/J mouse carrying an implanted C1300 neuroblastoma tumor spheroid. Complex changes were observed in the blood flow of the microvascular system in the tumor, but not in nearby vessels in the skin. More specifically, there was a general slowing of the rate of blood flow in the tumor and significant and selective changes in vascular permeability, including plasma leakage into the extravascular space and hemorrhage. No similar effects were evident on nearby vessels in skin or in nearby angiogenic vessels that were formed in response to surgical damage to the skin at the edges of the chamber. These results demonstrate that a CDFE selectively alters the permeability of blood vessels associated with a tumor.

The effect of NV144, alone or in combination with a chemotherapeutic agent, was examined using the syngeneic MAT B III rat breast carcinoma model system. The MAT B III rat breast carcinoma is very malignant and fast-growing and, unlike many animal tumors, metastasizes. In addition, the tumor-bearing host lives sufficiently long to develop metastatic disease from the primary tumor. As such, the MAT-BIII tumor model has similar characteristics to human tumors.

Fisher 344 rats bearing MAT B III breast carcinoma tumors were used for these studies. Experiments were begun when the tumors reached approximately 170–200 mm3 in size (5–9 days; "day 0"). Tumors in saline treated controls grew very rapidly and reach a size of about 35,000 $mm^3$ at day 7. In the treatment groups, tumor-bearing rats were treated with NV144 or DOXIL (Sequus Pharmaceuticals, Inc.), either alone or in combination. In the clinic, DOXIL generally is administered at about 4 mg/kg. In various experiments as disclosed herein, DOXIL was administered by intravenous injection at doses of 1, 2, 4 or 9 mg/kg, at days 0, 7 and 14, either alone or with NV144. NV144 has no significant anti-tumor activity when administered alone.

In a dose-response experiment, 2 mg/kg DOXIL was administered intravenously in combination with 0.4, 1.3, 4 or 12 mg/kg NV144 at days 0, 7 and 14, and tumor size was determined using a caliper. Tumor growth was similar in all groups until day 28, when tumors in mice treated with DOXIL and either 4 or 12 mg/kg NV144 showed a decrease in tumor size. Based on these studies, 4 mg/kg NV144 was used in further experiments.

Figure 2:
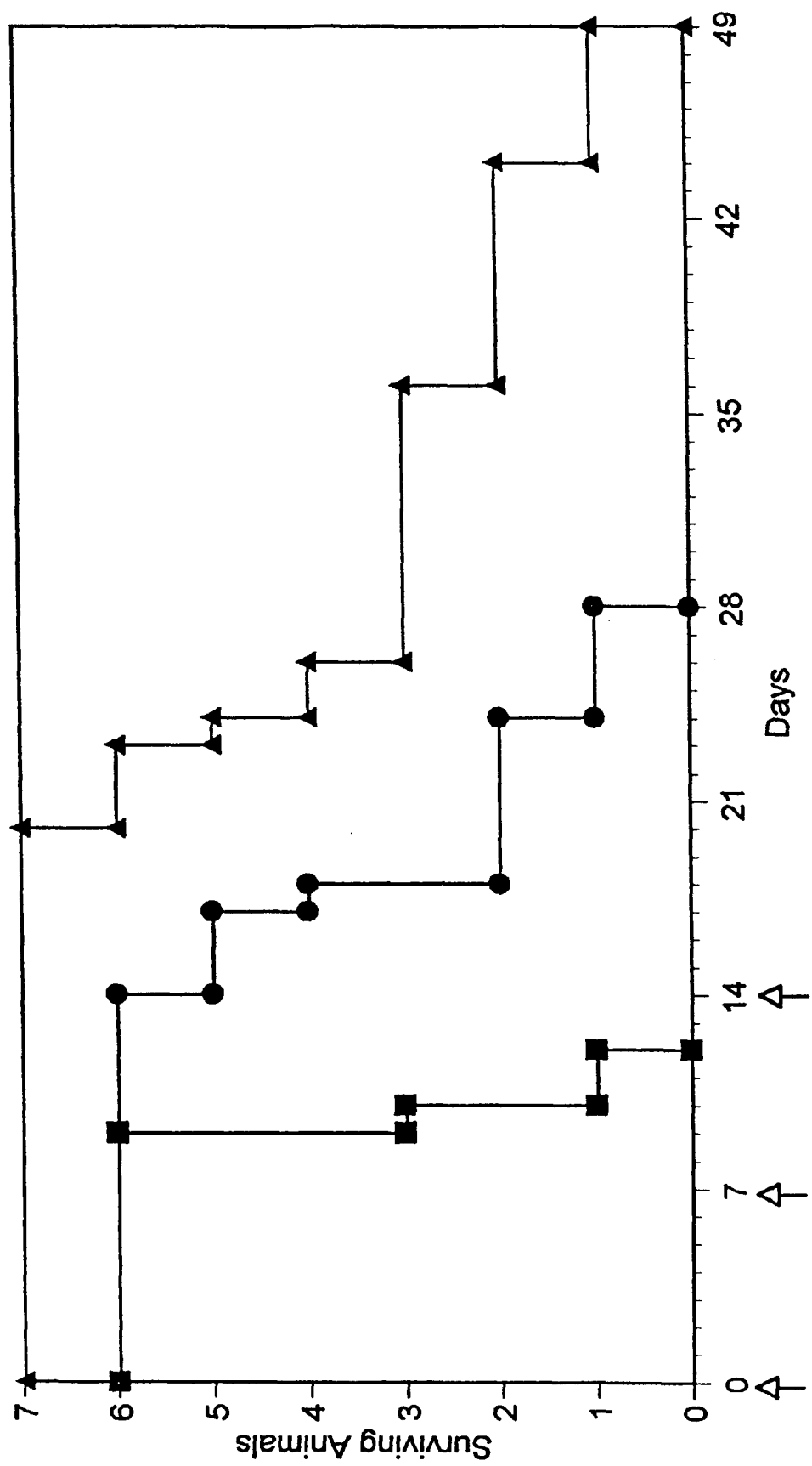
FIG. 2 shows the survival of MAT-BIII breast carcinoma tumor-bearing Fisher 344 rats at various times following administration of saline (squares), 2 mg/kg DOXIL plus saline (circles), or 2 mg/kg DOXIL plus 4 mg/kg NV144 (triangles). DOXIL is "stealth" liposome that contains doxorubicin (Sequus Pharmaceuticals, Inc.; Menlo Park Calif.). Animals were treated at days 0, 7 and 14, as indicated by the arrows.

In various experiments, tumor-bearing rats were treated with 1, 2 or 9 mg/kg DOXIL, alone or in combination with 4 mg/kg NV144. In all experiments, decreased tumor growth rates were observed in rats treated with the combination therapy as compared to those treated only with DOXIL. In addition, tumor sizes decreased to a greater extent in rats treated with the combination therapy. Furthermore, rats treated with 2 mg/kg DOXIL and 4 mg/kg NV144 had a much greater survival than those treated only with 2 mg/kg DOXIL, including one animal that remained alive beyond the 7 week observation period (FIG. 2) and appeared to be free of any tumor. At the highest dose of DOXIL (9 mg/kg), survival initially appeared to be similar in both groups of rats; however, none of the animals survived beyond day 23 due to the high dose of DOXIL.

These results demonstrate that administration of a CDFE with a chemotherapeutic agent enhanced the efficacy of the chemotherapeutic agent. In particular, the effect produced by the combination of CDFE and DOXIL produced a greater than additive effect.

Although the invention has been described with reference to the above examples, it will be understood that modifications and variations are encompassed within the spirit and scope of the invention. Accordingly, the invention is limited only by the following claims.

What is claimed is:

1. A method of enhancing the efficacy of a cancer chemotherapeutic agent in a subject, the method comprising administering the cancer chemotherapeutic agent and a context-dependent functional entity (CDFE) to a subject having a tumor, said context-dependent functional entity comprising a coagulation factor selected from tissue factor (TF) and a modified form of TF having thrombogenic activity operably linked to a kringle 5 domain, whereby the CDFE increases permeability of tumor-associated vascular tissue, thereby enhancing the efficacy of the chemotherapeutic agent.

2. A method of enhancing the efficacy of doxorubicin a subject, the method comprising administering the doxorubicin and a context-dependent functional entity (CDFE) to a subject having a tumor, said context-dependent functional entity comprising a truncated tissue factor (TF) operably linked to a kringle 5 domain, wherein the truncated TF comprises, amino acids 35 to 243 of human TF, and the kringle 5 domain comprises Pro-Arg-Lys-Leu-Tyr-Asp (SEQ ID NO: 1), whereby the CDFE increases permeability of tumor-associated vascular tissue, thereby enhancing the efficacy of the doxorubicin.

3. The method of claim 2, wherein the truncated TF and kringle 5 domain are operably linked through a spacer peptide having the amino acid sequence:

Gly-Gly-Gly-Gly-Ser-Gly-Gly-Gly-Gly-Ser-Gly-Gly-Gly-Gly-Ser (SEQ ID NO: 3).

4. The method of claim 1, wherein the TF is a vertebrate TF.

5. The method of claim 4, wherein the vertebrate TF is human TF.

6. The method of claim 5, wherein the modified form of TF comprises a polypeptide comprising amino acids 35 to 243 of human TF.

7. The method of claim 1, wherein the kringle domain comprises a kringle 5 domain.

8. The method of claim 17, wherein the selective recognition domain comprises the amino acid sequence: Pro-Arg-Lys-Leu-Tyr-Asp (SEQ ID NO: 1).

9. The method of claim 1, wherein the tissue factor (TF) or and modified form of TF and kringle domain are operably linked through a spacer peptide.

10. The method of claim 9, wherein the spacer peptide has the amino acid sequence:

Gly-Gly-Gly-Gly-Ser-Gly-Gly-Gly-Gly-Ser-Gly-Gly-Gly-Gly-Ser (SEQ ID NO: 3).

11. The method of claim 1, wherein the cancer chemotherapeutic agent is selected from the group consisting of an antimetabolite, an alkylating agent, an antitumor antibiotic, a cytokine, a hormone, a hormone antagonist, a nitroso compound, a plant alkaloid, and a platinum compound.

12. The method of claim 1, wherein the cancer chemotherapeutic agent is an anthracycline.

13. The method of claim 1, wherein the anthracycline is doxorubicin.

14. The method of claim 1, wherein the agent is in an encapsulating medium.

15. The method of claim 14, wherein the encapsulating medium is a liposome.

16. The method of claim 15, wherein the liposome is a modified liposome.

17. The method of claim 15, wherein the agent is a cancer chemotherapeutic agent.

18. The method of claim 15, wherein the agent is doxorubicin.

19. The method of claim 1, wherein the cancer chemotherapeutic agent and the context-dependent functional entity are administered in combination.

20. The method of claim 1, wherein the cancer chemotherapeutic agent and the context-dependent functional entity are administered sequentially.

21. The method of claim 1, wherein the cancer chemotherapeutic agent and the context-dependent functional entity are administered parenterally.

22. The method of claim 1, wherein the cancer chemotherapeutic agent and the context-dependent functional entity are administered intravenously.

23. The method of claim 1, wherein the cancer chemotherapeutic agent and the context-dependent functional entity are administered orally.

24. The method of claim 1, wherein the cancer chemotherapeutic agent and the context-dependent functional entity are administered at the site of the tissue.

* * * * *